(12) United States Patent
Fain et al.

(10) Patent No.: US 9,763,597 B2
(45) Date of Patent: Sep. 19, 2017

(54) LOCAL MRI BREAST COIL AND METHOD OF USE

(75) Inventors: Sean Bedilion Fain, Madison, WI (US); Krishna N. Kuprad, Madison, WI (US); Xu Zhai, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 2004 days.

(21) Appl. No.: 12/108,070

(22) Filed: Apr. 23, 2008

(65) Prior Publication Data

US 2008/0275333 A1   Nov. 6, 2008

Related U.S. Application Data

(60) Provisional application No. 60/915,842, filed on May 3, 2007.

(51) Int. Cl.
*A61B 5/05*         (2006.01)
*A61B 5/055*        (2006.01)
*G01R 33/34*        (2006.01)
*G01R 33/341*       (2006.01)
*G01R 33/3415*      (2006.01)

(52) U.S. Cl.
CPC ............ *A61B 5/055* (2013.01); *G01R 33/341* (2013.01); *G01R 33/3415* (2013.01); *G01R 33/34046* (2013.01); *G01R 33/34053* (2013.01)

(58) Field of Classification Search
CPC ........ G01R 33/34046; G01R 33/34053; G01R 33/341; G01R 33/3415; A61B 5/055; A61B 2019/205; A61B 10/0041; A61B 5/05

USPC ......... 600/410, 422; 324/307, 309, 318, 322
See application file for complete search history.

(56) References Cited

U.S. PATENT DOCUMENTS

| | | | |
|---|---|---|---|
| 5,363,845 A | 11/1994 | Chowdhury et al. | |
| 5,706,812 A | 1/1998 | Strenk et al. | |
| 6,023,166 A * | 2/2000 | Eydelman | 324/318 |
| 6,087,832 A | 7/2000 | Doty | |
| 6,163,717 A | 12/2000 | Su | |
| 6,198,962 B1 * | 3/2001 | Su | 600/422 |
| 6,701,178 B2 * | 3/2004 | Su et al. | 600/422 |
| 2006/0201504 A1 | 9/2006 | Singhal et al. | |

OTHER PUBLICATIONS

Ling Sun et al; Design and Optimization of a Breast Coil for Magnetic Resonance Imaging; MRI, vol. 11, pp. 73-80; 1993.

* cited by examiner

*Primary Examiner* — Elmer Chao
(74) *Attorney, Agent, or Firm* — Quarles & Brady LLP

(57) ABSTRACT

A local breast coil is designed to be tightly coupled to the natural shape of the pendant breast to provide high SNR for diagnostic MR imaging applications, while still providing access for interventional procedures through openings in the coil. In accordance with one configuration, the coil has a symmetrical design, such that the coil can be rotated about the breast to position an opening in the coil proximate to a desired portion of the breast without incurring registration or other alignment or artifact errors due to inhomogeneous B1 excitation. Furthermore, the coil is designed to facilitate medial and lateral imaging of the breast. The coil is combined with a patient support system that facilitates rotation of the coil and interchangeability of the coil to match the configuration of the coil to the position of the breast being imaged.

12 Claims, 6 Drawing Sheets

LOCAL MRI BREAST COIL AND METHOD OF USE

CROSS-REFERENCE TO RELATED APPLICATIONS

This application is based on, incorporates herein by reference, and claims the benefit of provisional application Ser. No. 60/915,842, filed May 3, 2007, and entitled "INTERVENTIONAL DEVICE WITH SOLENOID RF COIL."

STATEMENT REGARDING FEDERALLY SPONSORED RESEARCH

This invention was made with government support under Grant No. NIH 5 P30 CA014520-33. The United States Government has certain rights in this invention.

FIELD OF THE INVENTION

The invention relates to a system and method for imaging a breast using a magnetic resonance imaging (MRI) system. More particularly, a local breast coil is provided that enables medial and lateral imaging of the breast and provides ready access to the breast throughout the imaging process.

BACKGROUND OF THE INVENTION

Breast cancer is a fatal disease caused by the growth of cancerous cells within breast tissue. These cancerous cells form a lump, cyst, lesion, and the like that can grow at an alarming rate and, if left undetected, can even spread beyond the breast. Unfortunately, even with an increasing number of breast cancer cases reported each year, many women are still reluctant to go in for scheduled examinations or to receive treatment for non-cancerous lumps. A major reason for this reluctance is the physical and psychological discomfort that are experienced during examinations and treatments.

For example, screening mammography has been one of the primary diagnosis tools for breast cancer detection for over 30 years. However, many women find the compression of the breast required during a mammography procedure to be extremely uncomfortable.

Though more costly than x-ray mammography, MRI is more sensitive and can be used to detect lesions at an earlier stage than traditional mammography. Furthermore, MRI of the breast does not require compression of the breast like mammography.

In basic principle, when a substance such as human tissue is subjected to a uniform magnetic field (polarizing field $B_0$) applied along an axis, typically designated the z axis of a Cartesian coordinate system, the individual magnetic moments of the spins in the tissue attempt to align with this polarizing field, but precess about it in random order at their characteristic Larmor frequency. If the substance, or tissue, is subjected to a magnetic field (excitation field $B_1$) that is in a perpendicular plane to the axis, typically designated the x-y plane, and that is near the Larmor frequency, the net aligned moment, $M_z$, may be rotated, or "tipped", into that x-y plane to produce a net transverse magnetic moment $M_t$. A nuclear magnetic resonance (NMR) signal is emitted by the excited spins after the excitation signal $B_1$ is terminated. This NMR signal may be received and processed to form an image or produce a spectrum.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

Radio frequency antennas, or coils, are used to produce the excitation field $B_1$ and other RF magnetic fields in the subject being examined. Such coils are also used to receive the very weak NMR signals that are produced in the subject. Such coils may be so-called "whole body" coils that are large enough to produce a uniform magnetic field for a human subject or, they can be much smaller "local" coils that are designed for specific clinical applications such as head imaging, knee imaging, wrist imaging, breast imaging, and the like.

In the case of breast MRI, a local breast coil is typically employed. Typically, to arrange the breast in the coil, the woman is arranged in the prone position and the breast positioned in a local coil arranged beneath a patient bed on which the woman is laying. Thus, the breast is not compressed.

Two types of local coils are typically utilized in breast imaging and each coil design has an associated number of advantages and drawbacks. One coil type is often referred to as an "open" coil. These coils have coil elements that are arranged about an area where the breast is arranged but are disposed at a distance from the actual breast. These open coils provide ready access to the breast when it is arranged in the coil to facilitate stereotactic procedures, allow the placement of fiducial markers, and the like. Unfortunately, the distance between the exterior of the breast and the location of the coil reduces the signal-to-noise ratio (SNR). That is, the further the coil is decoupled from the breast, the lower the SNR To improve SNR, some traditional local breast coils utilize a "saddle" design that is built into a frame that extends below the patient bed. In this regard, the coil is arranged directly about the breast. While this configuration increases SNR, these traditional saddle coils present a number of drawbacks. Specifically, the amount of access to the breast when arranged in the coil is significantly restricted. That is, saddle coils can only be rotated about the principal magnetic field (z) axis without seriously compromising SNR. For biopsy, rotation about z axis is done to improve access and visualization of the target region, but this rotation is highly constrained and limited to only a few degrees of rotation.

Therefore, it would be desirable to have a system and method for imaging a breast using an MRI system that permits ready access to any desired portion of the breast when the breast is positioned in the local coil while still providing a high SNR and not requiring an onerous registration or orientation process.

SUMMARY OF THE INVENTION

The present invention overcomes the aforementioned drawbacks by providing a local breast coil that is designed to be tightly coupled to the breast to provide high SNR, while still providing access to the breast through openings in the coil. The coil has a symmetrical design, such that the coil is well suited to transmit/receive rather than receive only configurations and thus can readily be used for bilateral imaging of the breast with minimized cross-talk and improved and reduced noise. In accordance with one configuration, the coil can be rotated about the breast to position an opening in the coil proximate to a desired portion of the breast without incurring registration or other alignment or artifact errors due to inhomogeneous B1 excitation. Furthermore, the coil is designed to facilitate medial and lateral imaging of the breast with good sensitivity in regions proximal to the chest wall.

In accordance with one aspect of the invention, an RF coil for use with a magnetic resonance imaging (MRI) system is disclosed that includes a frame and a conductor coupled to the frame and extending about the frame to form a solenoid shape. The frame includes an opening at a first end having a first cross-sectional area configured to receive a body part to be imaged using the MRI system and a frame body extending along a central axis of the frame from the first end toward a second end having a second cross-sectional area smaller than the first cross sectional area. The frame also includes a plurality of openings formed in the frame body to provide access from an exterior of the frame body to the body part arranged in an interior of the frame. The conductor includes a first loop arranged proximate to the first end of the frame and extending in a first plane substantially transverse to the central axis of the frame and a second loop arranged proximate to the second end of the frame and extending in a second plane substantially parallel to the first plane and transverse to the central axis of the frame. The conductor also includes at least one leg connecting the first loop and the second loop. Accordingly, at least a portion of the plurality of openings formed in the frame body is accessible between the first loop and the second loop.

In accordance with another aspect of the invention, a patient support system configured to support a patient during an MRI process using an MRI system is disclosed that includes a bed having a surface configured to receive the patient to support the patient during the MRI process and an RF coil as described above.

Various other features of the present invention will be made apparent from the following detailed description and the drawings.

DETAILED DESCRIPTION OF THE INVENTION

Figure 1:
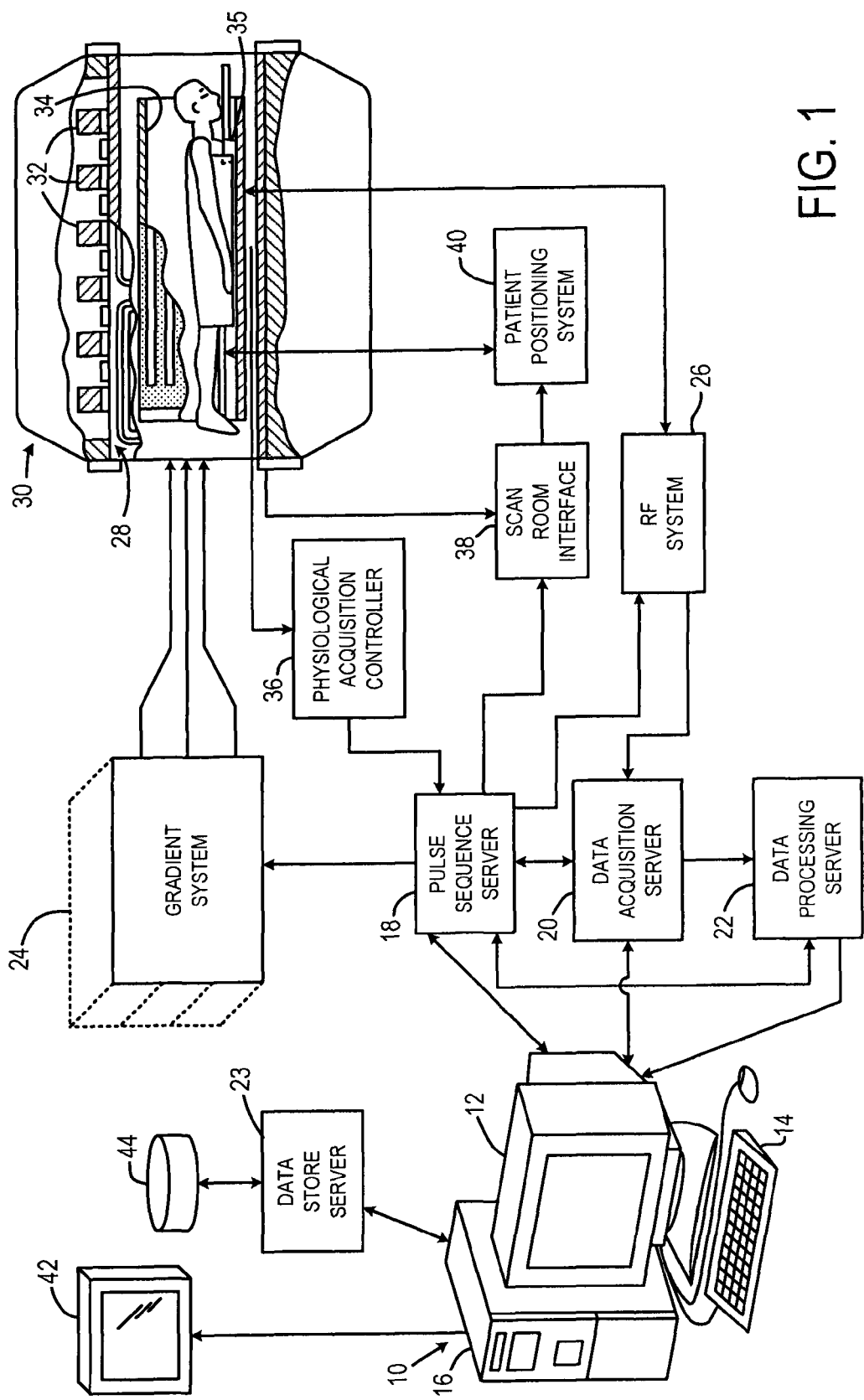
FIG. 1 is a block diagram of an MRI system that employs the present invention.

Referring particularly to FIG. 1, the present invention is employed with an MRI system. The MRI system includes a workstation 10 having a display 12 and a keyboard 14. The workstation 10 includes a processor 16 that is a commercially available programmable machine running a commercially available operating system. The workstation 10 provides the operator interface that enables scan prescriptions to be entered into the MRI system. The workstation 10 is coupled to, for example, four servers including a pulse sequence server 18, a data acquisition server 20, a data processing server 22, and a data store server 23. The workstation 10 and each server 18, 20, 22 and 23 are connected to communicate with each other.

The pulse sequence server 18 functions in response to instructions downloaded from the workstation 10 to operate a gradient system 24 and an RF system 26. Gradient waveforms necessary to perform the prescribed scan are produced and applied to the gradient system 24 that excites gradient coils in an assembly 28 to produce the magnetic field gradients $G_x$, $G_y$, and $G_z$ used for position encoding MR signals. The gradient coil assembly 28 forms part of a magnet assembly 30 that includes a polarizing magnet 32 and a whole-body RF coil 34 or, in accordance with the present invention, a local RF coil 35.

In operation, RF excitation waveforms are applied to the RF coil 34 by the RF system 26 to perform the prescribed magnetic resonance pulse sequence. Responsive MR signals are detected by, as will be described, a local RF coil 35. The MR signals are received and provided to the RF system 26 where, as will be described with respect to FIG. 2, the signals are amplified, demodulated, filtered, and digitized under direction of commands produced by the pulse sequence server 18.

The RF system 26 includes an RF transmitter for producing a wide variety of RF pulses used in MR pulse sequences. The RF transmitter is responsive to the scan prescription and direction from the pulse sequence server 18 to produce RF pulses of the desired frequency, phase and pulse amplitude waveform. The generated RF pulses may be applied to the whole body RF coil 34 or to one or more local coils or coil arrays 35. As will be described, it is contemplated that the local coil 35 in accordance with the present invention may be used as both a receive and a transmit coil.

The RF system 26 also includes one or more RF receiver channels. Each RF receiver channel includes an RF amplifier that amplifies the MR signal received by the coil to which it is connected and a detector that detects and digitizes the I and Q quadrature components of the received MR signal. The magnitude of the received MR signal may thus be determined at any sampled point by the square root of the sum of the squares of the I and Q components:

$$M=\sqrt{I^2+Q^2},$$

and the phase of the received MR signal may also be determined:

$$\phi=\tan^{-1} Q/I.$$

The pulse sequence server 18 also optionally receives patient data from a physiological acquisition controller 36. The controller 36 receives signals from a number of different sensors connected to the patient, such as ECG signals from electrodes or respiratory signals from a bellows. Such signals are typically used by the pulse sequence server 18 to synchronize, or "gate", the performance of the scan with the subject's respiration or heart beat.

The pulse sequence server 18 also connects to a scan room interface circuit 38 that receives signals from various sensors associated with the condition of the patient and the magnet system. It is also through the scan room interface circuit 38 that a patient positioning system 40 receives commands to move the patient to desired positions during the scan.

The digitized MR signal samples produced by the RF system 26 are received by the data acquisition server 20. The data acquisition server 20 operates in response to instructions downloaded from the workstation 10 to receive the real-time MR data and provide buffer storage such that no data is lost by data overrun. In some scans, the data acquisition server 20 does little more than pass the acquired MR data to the data processor server 22. However, in scans that require information derived from acquired MR data to control the further performance of the scan, the data acquisition server 20 is programmed to produce such information and convey it to the pulse sequence server 18. For example, during pre-scans MR data is acquired and used to calibrate the pulse sequence performed by the pulse sequence server 18. Also, navigator signals may be acquired during a scan and used to adjust RF or gradient system operating parameters or to control the view order in which k-space is sampled. And, the data acquisition server 20 may be employed to process MR signals used to detect the arrival of contrast agent in an MRA scan. In all these examples the data acquisition server 20 acquires MR data and processes it in real-time to produce information that is used to control the scan.

The data processing server 22 receives MR data from the data acquisition server 20 and processes it in accordance with instructions downloaded from the workstation 10. Such processing may include, for example: Fourier transformation of raw k-space MR data to produce two or three-dimensional images; the application of filters to a reconstructed image; the performance of a backprojection image reconstruction of acquired MR data; the calculation of functional MR images; the calculation of motion or flow images, etc.

Images reconstructed by the data processing server 22 are conveyed back to the workstation 10 where they are stored. Real-time images are stored in a data base memory cache (not shown) from which they may be output to operator display 12 or a display that is located near the magnet assembly 30 for use by attending physicians. Batch mode images or selected real time images are stored in a host database on disc storage 44. When such images have been reconstructed and transferred to storage, the data processing server 22 notifies the data store server 23 on the workstation 10. The workstation 10 may be used by an operator to archive the images, produce films, or send the images via a network to other facilities.

Figure 2:
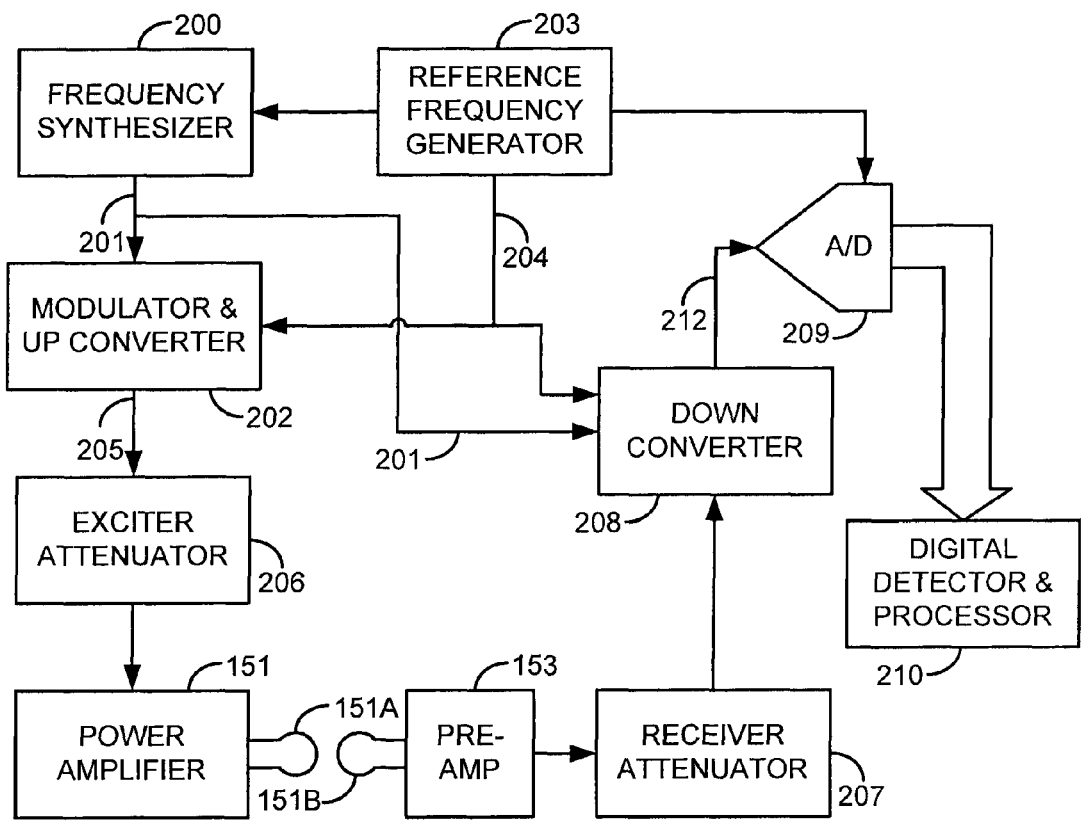
FIG. 2 is a block diagram of an RF system that forms part of the MRI system of FIG. 1.

As shown in FIG. 1, the RF system 26 may be connected to the whole body RF coil 34 or local coil 35, or as shown in FIG. 2, a transmitter section of the RF system 26 may connect to one RF coil 152A and its receiver section may connect to a separate RF receive coil 152B. Often, the transmitter section is connected to the whole body RF coil 34 and each receiver section is connected to separate local coils 35, 152B. In addition, as will be described, it is contemplated that the transmit RF coil 152A and the receive RF coil 152B may be the same local coil 35 described above with respect to FIG. 1.

Referring particularly to FIG. 2, the RF system 26 includes a transmitter that produces a prescribed RF excitation field. The base, or carrier, frequency of this RF excitation field is produced under control of a frequency synthesizer 200 that receives a set of digital signals from the pulse sequence server 18. These digital signals indicate the frequency and phase of the RF carrier signal produced at an output 201. The RF carrier is applied to a modulator and up converter 202 where its amplitude is modulated in response to a signal R(t) also received from the pulse sequence server 18. The signal R(t) defines the envelope of the RF excitation pulse to be produced and is produced by sequentially reading out a series of stored digital values. These stored digital values may, be changed to enable any desired RF pulse envelope to be produced.

The magnitude of the RF excitation pulse produced at output 205 is attenuated by an exciter attenuator circuit 206 that receives a digital command from the pulse sequence server 18. The attenuated RF excitation pulses are applied to the power amplifier 151 that drives the transmit RF coil 152A.

Referring still to FIG. 2, the signal produced by the subject is picked up by the receive RF coil 152B, which, again, may be the same physical coil as the transmit RF coil 152A. The received MR signals are applied through a preamplifier 153 to the input of a receiver attenuator 207. The receiver attenuator 207 further amplifies the signal by an amount determined by a digital attenuation signal received from the pulse sequence server 18. The received signal is at or around the Larmor frequency, and this high frequency signal is down converted in a two step process by a down converter 208 that first mixes the MR signal with the carrier signal on line 201 and then mixes the resulting difference signal with a reference signal on line 204. The down converted MR signal is applied to the input of an analog-to-digital (A/D) converter 209 that samples and digitizes the analog signal and applies it to a digital detector and signal processor 210 that produces 16-bit in-phase (I) values and 16-bit quadrature (Q) values corresponding to the received signal. The resulting stream of digitized I and Q values of the received signal are output to the data acquisition server 20. The reference signal as well as the sampling signal applied to the A/D converter 209 are produced by a reference frequency generator 203.

Figure 3:
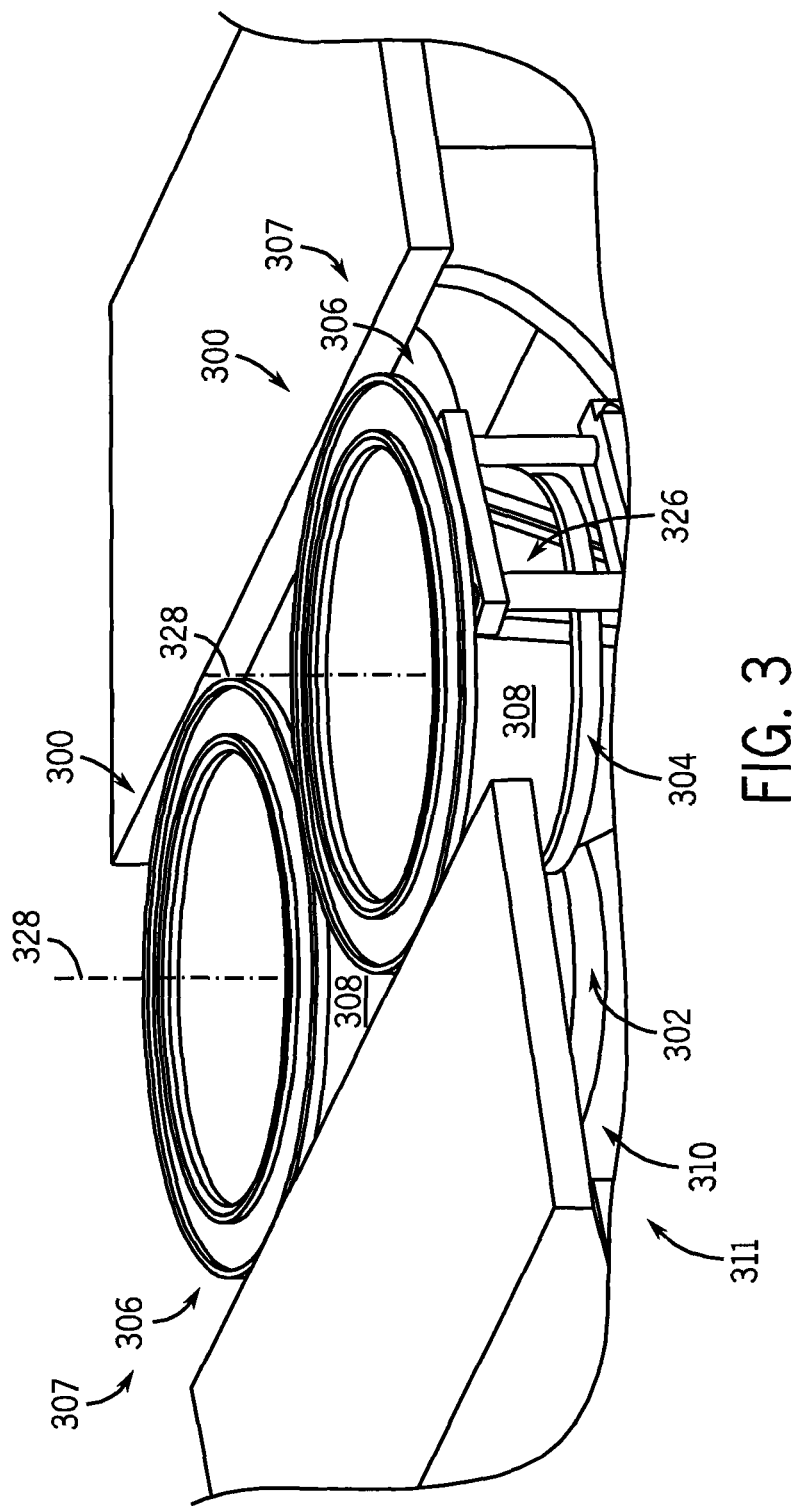
FIG. 3 is a perspective view of a local breast coil in accordance with the present invention and utilized with the systems of FIGS. 1 and 2.
Figure 4:
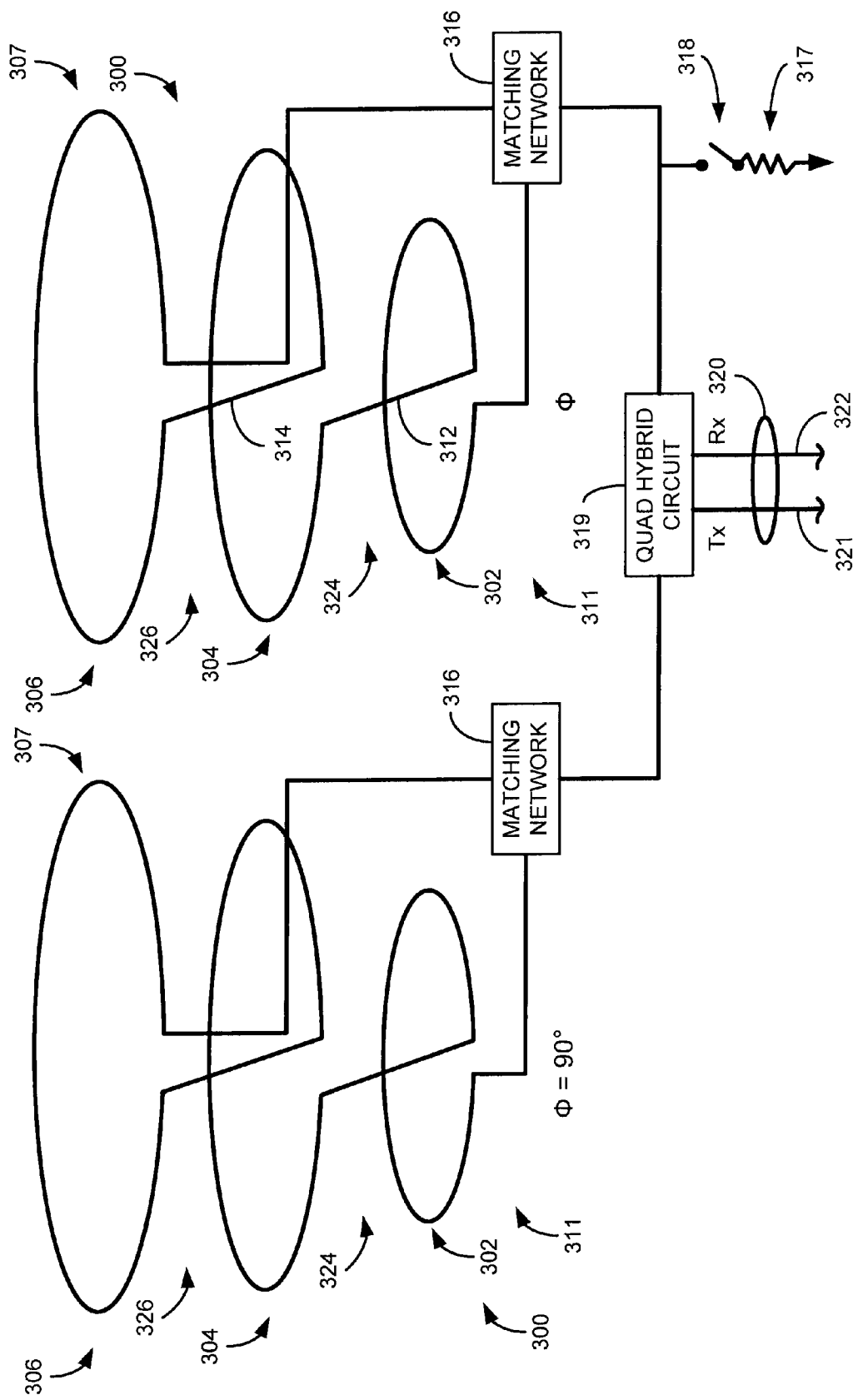
FIG. 4 is a schematic diagram of a conductor arrangement of the coil of FIG. 3.
Figure 5:
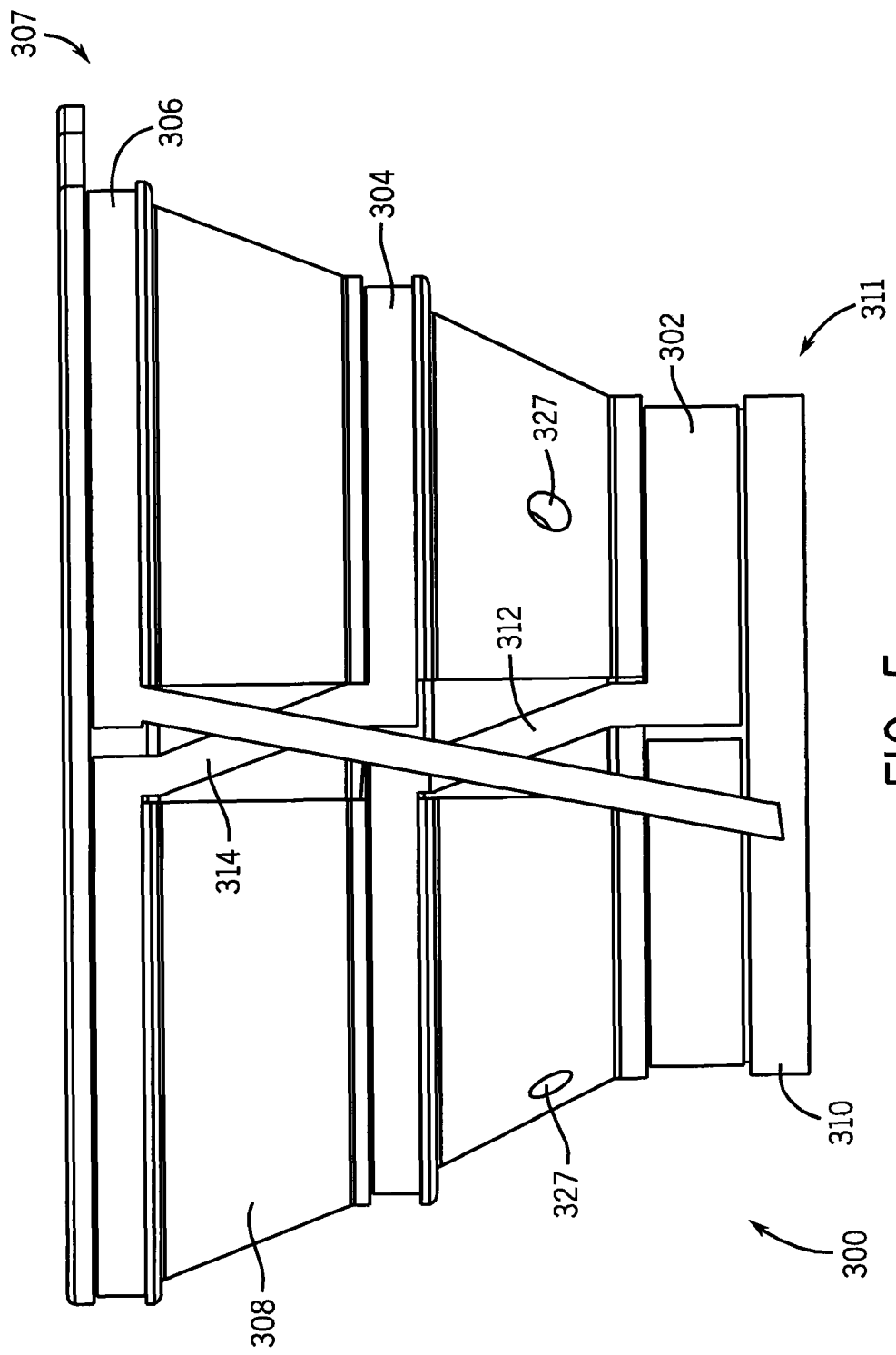
FIG. 5 is a side-elevational view of a conductor arrangement of the coil of FIGS. 3 and 4.

Referring now to FIGS. 3, 4, and 5, a local breast coil 300 having a solenoid shape in accordance with the present invention includes a first turn or loop 302, a second turn or loop 304, and third turn or loop 306. It is contemplated that the RF coil 300 may include any other number of loops. That is, the RF coil 300 could have any number of windings and the specific number of windings can be optimized depending on the imaging and intervention requirements.

The first loop 302, second loop 304, and third loop 306 are mounted to a cup-shaped frame 308. It is noted that the first loop 302 is mounted proximate a first end 307 of the frame 308. Accordingly, the RF coil 300 is designed to provide substantial sensitivity extending into the chest wall due to its close proximity to the chest wall when a patient is arranged in the prone position illustrated in FIG. 1

As used herein, the term "mount" can include join, unite, connect, associate, insert, hang, hold, affix, attach, fasten, bind, paste, secure, bolt, nail, glue, screw, rivet, solder, weld, and other like terms. The loops of the RF coil 300 may be made of copper or any other conducting material known to those of skill in the art. In accordance with one configuration, the loops of the RF coil 300 can be in the form of conducting strips or ribbons, such as thin strips of a conducting material. Alternatively, the loops can be in the form of conducting wires or any other conducting segments.

As used herein, a 'cup-shaped' frame can refer to any frame with a concave inner surface adapted to receive a body part such as a breast. The inner surface of the cup-shaped frame can be circular, elliptical, cylindrical, or any other cup-like shape adapted to receive the body part. Alternatively, the cup-shaped frame can refer to a plurality of frames arranged to form a concave inner surface for receiving a breast. The cup-shaped frame can also come in different sizes to accommodate patients of different sizes.

As illustrated, The RF coil 300 is mounted to cup-shaped frame 308 such that the each loop 302, 304, 306 lie in respective planes that are substantially parallel to each other and a plane formed by a base 310 the RF coil 300 arranged at a second end 311 opposite the first end 307 of the frame 308. Furthermore, as will be described, the respective planes of each loop 302, 304, 306 extend transverse or perpendicular to a central axis 328 extending through the frame 308.

While it is contemplated that the conductors 302, 304, 306 may be mounted in other orientations relative to cup-shaped frame 308, it is noted that the orientations illustrated in FIGS. 3-5 are desirable due to the high degree of regularity and homogeneity in the magnetic field produced by the coil 300. Nonetheless, as will be described with respect to FIG. 7, a conductor may be arranged in a saddle configuration. Furthermore, it is contemplated that a loop may include a conducting strip with two faces and two sides. The conducting strip can be mounted horizontally such that a face of the conducting strip lies in a plane that is substantially parallel to the base 310. Alternatively, the conducting strip can be mounted vertically such that a side of the conducting strip lies in the plane that is substantially parallel to the base 310. In yet another embodiment, the loop may be implemented with a copper wire or cylindrical copper tube. In one configuration, the cup-shaped frame 308 can include one or more ledges adapted to receive the loops of the RF coil 300.

Referring back to FIGS. 3, 4, and 5, the loops 302, 304, 306 of the RF coil 300 are mounted as spaced concentric shapes that substantially conform to an outer surface of cup-shaped frame 308. The outer surface of the cup-shaped frame 308 can have a circular or ovular shape such that the loops 302, 304, 306 of the RF coil 300 form concentric circles that are designed to be coupled tightly to the breast. Alternatively, the outer surface of the cup-shaped frame 308 can take other shapes including various tapers that are linear or non-linear and the loops 302, 304, 306 of the solenoid RF coil can be shaped accordingly. In an alternative configuration, the shape of the loops 302, 304, 306 may be different from that of the outer surface of the cup-shaped frame 308. For example, the outer surface of the cup-shaped frame 308 may be square, and the loops 302, 304, 306 of the RF coil 300 may be circular. Further still, the loops 302, 304, 306 of the RF coil 300 may be mounted to the cup-shaped frame 308 in other configurations. For example, the loops may be mounted such that one or more of the loops 302, 304, 306 lie in planes that are not substantially parallel to the base 310. Also, the loops may be mounted to an inner surface of the cup-shaped frame 308.

In one configuration, spacing between the loops of the RF coil 300 can be equidistant such that a distance between the first loop 302 and second loop 304 are the same as a distance between the second loop 304 and third loop 306. Alternatively, the spacing between loops 302, 304, 306 may be unequal. In an exemplary configuration, consecutive loops of the solenoid RF coil 300 can be connected by respective conducting coil legs 312, 314 such that the RF coil 300 is continuous along its length. Thus, the loops 302, 304, 306 are connected electrically in series to form a solenoid.

In particular a single continuous conductor, for example, a copper conductor forms the loops 302, 304, 306 and legs 312, 324 and extends along the surface of the cup-shaped frame 308. The specific shape, size, and dimensions of the cup-shaped frame 308 may vary such that a number of RF coils 300 may be selected from to adjust the size parameters to optimally accommodate a range of breast sizes. To this end, although three loops 302, 304, 306 are illustrated, it is contemplated that more loops of the conductor may be desirable depending on the size of the breast to be imaged and the application being performed.

The solenoidal geometry of this conductive strip provides homogenous B1 excitation and reception fields, while the tapering of the solenoid near the nipple of the breast allows more efficient coupling to the breast tissue for improved signal to noise (SNR). This tapering of the coil diameter or cross-section is best illustrated in FIGS. 4 and 5, which show that the cross-sectional area inside each subsequent loop extending further from the first end 307 of the frame 308 toward a second end 311 of the frame 308 decreases. The following table provides evidence of the SNR performance of the above-described coil using a conventional T1-weighted gradient recalled echo acquisition commonly used for diagnostic breast MRI in comparison to other, local receive coils of conventional design.

| Region | Solenoid Coil | 7 Channel Coil | 4 Channel Coil |
| --- | --- | --- | --- |
| Upper | 9.6 | 8.9 | 11.9 |
| Middle | 21.9 | 10.0 | 13.0 |
| Lower | 54.1 | 10.4 | 16.0 |

Moreover, the orientation of the breast anatomy for the typically prone patient position with respect to the principal magnetic field is preferable for this design because the primary axis of excitation field is transverse to the principal field, and thus is parallel to the axis of the solenoid. This arrangement provides good isolation between the two coils and allows the RF coil 300 to be designed as a transmit/receive coil or as a receive-only coil.

Referring to FIG. 4, a pair of solenoid RF coils 300 is shown. Each RF coil 300 includes a tuning module 316. In one configuration, the tuning module 316 can be in electrical communication with solenoid RF coil 300 and located proximate to a base 310 of the RF coil 300. The tuning module 316 may include a matching capacitor and a tuning capacitor such that solenoid RF coil 300 can be matched and tuned as known to those of skill in the art. Alternatively, the tuning module 316 can include any other components capable of matching and/or tuning solenoid RF coil 300.

A resistive load 317 with a switch 318 is provided to allow switching between unilateral and bilateral operation if bilateral operation is not needed. Furthermore, a quad hybrid circuit 319 allows excitation-reception of each coil with orthogonal phase between them for separation of the received signals and improved isolation beyond that already provided by the geometrical advantages described above.

A coaxial cable 320 can be used to connect the solenoid RF coil 300 with the MRI system, such as described with respect to FIG. 1. The coaxial cable may include a transmit line 321 and a receive line 322. Accordingly, in operation, the RF coil 300 can be used with the MRI system to direct an RF pulse toward a body part that is placed in cup-shaped frame 308. Furthermore, the RF coil 300 may only be used to receive the resulting NMR signals.

During this process or at any time when the breast is located within the RF coil 300, it is contemplated that the breast may be accessed via a lower window 324 or an upper window 326 of cup-shaped frame 308. These windows 324, 326 provide access for a biopsy/therapy probe (not shown) to access the breast tissue. The lower window 324 is positioned between the first loop 302 and second loop 306, and the upper window 326 is positioned between the second loop 304 and third loop 306. In configurations in which the RF coil 200 includes more loops, one or more windows may be provided between each pair of consecutive loops. The lower window 324 and/or upper window 326 can be apertures of any size or shape that allow unobstructed access to the breast or other body part arranged in the RF coil 300. Alternatively, either or both of the windows 324, 326 may include a plurality of apertures through which a medical device can be inserted.

Additionally, it is contemplated that more restricted windows may be provided in the cup-shaped frame 308. Specifically, referring to FIG. 5, it is contemplated that multiple portals 327 may be formed in the cup-shaped frame 308 to provide more restricted access to specific portions of the breast.

The symmetrical nature of the RF coil 300 provides a plurality of degrees of freedom such that unobstructed three-dimensional access to the breast through the RF coil 300 is provided. A first degree of freedom allows the RF coil 300 to be rotated bi-directionally in a complete circle. Specifically, a rotational axis 328 is created that is substantially perpendicular to the base 310 and that extends through a center of the cup-shaped frame 308.

Figure 6:
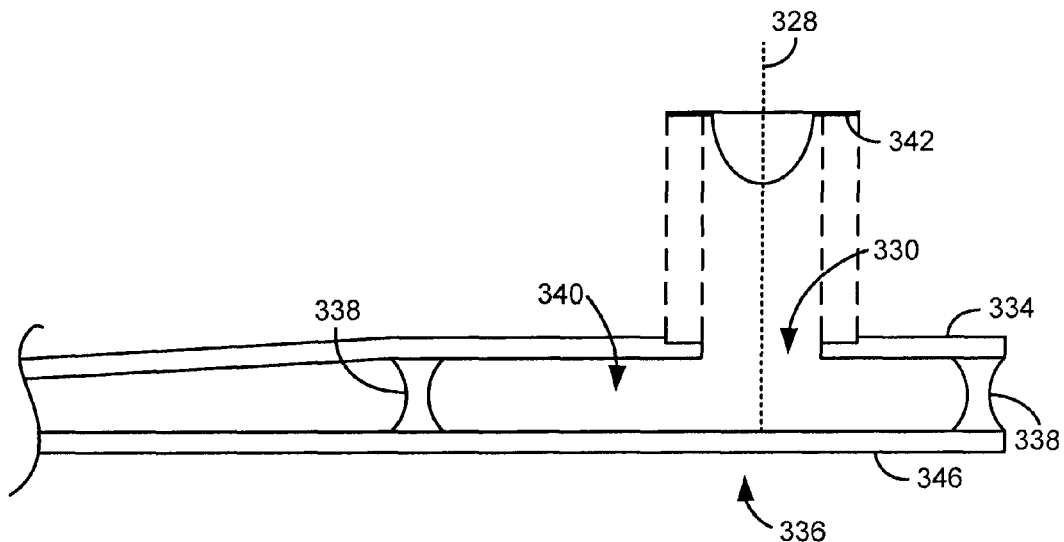
FIG. 6 is a side-elevational view of a patient table in accordance with the present invention that is designed to interchangeably receive local breast coils such as illustrated in FIG. 3.

Referring to FIG. 6, to facilitate such rotation, it is contemplated that the RF coil 300 may be coupled with a patient table 330 designed to receive the RF coil 300. Specifically, the patient table is designed to receive a patient in the prone position illustrated in FIG. 1. To this end, the patient table 300 includes a recess 332 configured to receive the RF coil 300. The recess is formed by providing a passage through an upper portion 334 of the patient table 330, such that the RF coil 300 may extend down through the upper portion 334 of the patient table 330 toward a lower portion 336 of the patient table 330. The upper portion 334 of the patient table 330 is separated from the lower portion 336 of the patient table 330 by a plurality of columns 338. This configuration not only provides a space 340 for the RF coil 300 to extend below the patient, but also provides a space within which the RF coil 300 can be accessed when in use. Accordingly, not only can the RF coil 300 be accessed during use, but the windows 324, 326 formed in the RF coil 300 provide a means of accessing the breast arranged within the RF coil during use.

It is also contemplated that the RF coil 300 may be removably coupled with the patient table 300 so that the size, dimension, and configuration of the RF coil 300 may be specifically matched to the patient. That is, the RF coil 300 is designed to engage the patient table through a mounting system that allows the RF coil 300 to be removed and replaced with relative ease. For example, the RF coil 300 may be secured to the patient bed 330 through the base 310 engaging the lower portion of the patient table 336. Additionally or alternatively, the RF coil 300 may include a mounting flange 342 that engages the upper portion 334 of the patient table 330.

As stated above, the RF coil 300 can be rotated about the rotational axis 328. To this end, it is contemplated that the RF coil 300 may be manually rotated to provide access to the desired portion of the breast through one or more of the windows 324, 326. Furthermore, rotation can be implemented through a rotation controller (not shown) that controls the relative position of the RF coil 300 with respect to the patient bed 330.

It should, however, be noted that the RF coil 300 described above allows a high degree of flexibility regarding the design of the patient support so as to optimally access the breast for diagnosis or therapy. In addition, the coils can be mounted on different sized holders so as to accommodate a range of breast sizes. Furthermore, by removing the close integration of the above-described electronics associated with the RF coil 300 from the patient table 330 support, it is possible to optimize both to improve access in the chest wall and medial regions without limiting the lateral access of conventional MR biopsy devices.

The above-described system provides a local breast coil 300 that is optimized for providing homogeneous excite/receive and is therefore well suited to bilateral imaging of breast tissue with minimal cross-talk and improved SNR. This underscores the general applicability of this design for both diagnostic and interventional applications. The design is based on a solenoid geometry that is symmetrical and tailored to conform to the breast shape for more efficient coupling to the tissue and improved SNR. To this end, image quality is not affected by rotating the coil. This is an advantageous feature because it allows the coil to be rotated to optimize the location for needle/probe or insertion for interventional procedures without interfering with the imaging process. Moreover, the combination of two such coils, one positioned on each breast, allows bilateral imaging with very efficient isolation of the signals from the right and left breast bilaterally. This provides a significant advantage for dynamic contrast-enhanced applications where bilateral coverage is desired with high spatial and temporal resolution imaging within a single injection of gadolinium contrast agent. Thus, the design is optimized for any region of the breast tissue intrinsically, well suited to transmit/receive and thus to bilateral imaging of the breast For diagnostic imaging, the design is superior to the receive only saddle designs from the point of view of symmetry, SNR, and access.

Figure 7:
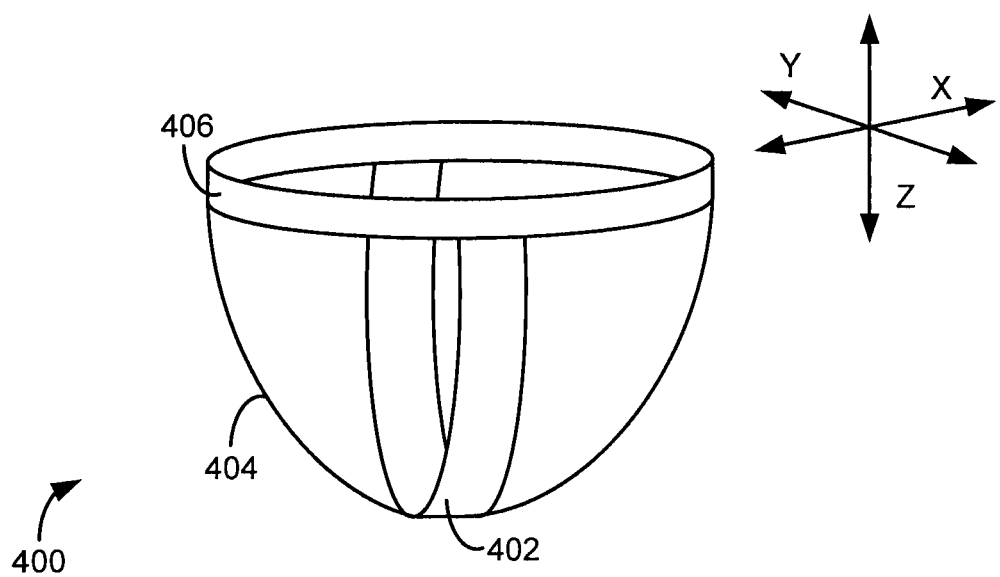
FIG. 7 is a perspective view of another conductor arrangement in accordance with the present invention.

Referring now to FIG. 7, another tapered local breast 400 coil design is provided. In this configuration, a strip of conductor 402 backed by a ground plane extends longitudinally about a cup-shaped frame 404. The strip conductor 402 forms one RF coil having a region of sensitivity along the x-axis. A second looped conductor 406 is placed around the circumference of a rim of the cup-shaped frame 404. The magnetic field due to looped conductor 406 extends perpendicular to the x-z plane and, hence, is orthogonal to the field due to the conductor strip 402. This arrangement ensures good isolation between the two conductors and may, hence, be designed as a transmit/receive coil or as a receive-only coil. However, this design does not have the rotational symmetry advantageously provided by the RF coil 300 described above. That is, unlike the coil 300 described above with respect to FIGS. 3-6, the coil design illustrated in FIG. 7 magnetic field of the strip conductor 400 won't remain perpendicular to the z-axis as the coil 400 is rotated.

The present invention has been described in terms of the various embodiments, and it should be appreciated that many equivalents, alternatives, variations, and modifications, aside from those expressly stated, are possible and within the scope of the invention. Therefore, the invention should not be limited to a particular described embodiment.

The invention claimed is:

1. A patient support system configured to support a patient during an MRI process using an MRI system, the patient support system comprising:
 a bed having a surface configured to receive the patient to support the patient during the MRI process;
 a first RF coil coupled to the bed comprising:
  a frame comprising:
   an opening at a first end having a first cross-sectional area configured to receive a body part to be imaged using the MRI system;

a frame body extending along a central axis of the frame from the first end toward a second end having a second cross-sectional area smaller than the first cross sectional area, the frame body rotatable about rotational axis extending along the central axis;

a plurality of openings formed in the frame body to provide access from an exterior of the frame body to the body part arranged in an interior of the frame;

a conductor coupled to the frame and extending about the frame to form a tapered solenoid shape comprising:

a first loop arranged proximate to the first end of the frame and extending in a first plane substantially transverse to the central axis of the frame;

a second loop arranged proximate to the second end of the frame and extending in a second plane substantially parallel to the first plane and transverse to the central axis of the frame;

at least one leg connecting the first loop and the second loop;

wherein at least a portion of the plurality of openings formed in the frame body is accessible between the first loop and the second loop;

wherein the conductor forming the solenoid shape and the frame body forming the plurality of openings are symmetrical about the central axis such that rotation of the frame body and conductor about the rotational axis does not incur registration and artifact errors due to inhomogeneous B1 excitation before and after rotation; and wherein the first coil is configured to operate as both a transmit coil and a receive coil and wherein the first coil creates a homogenous B1 excitation field and a homogenous reception field.

2. The patient support system of claim 1 further comprising a second RF coil coupled to the bed comprising, the second RF coil:

a frame comprising:

an opening at a first end having a first cross-sectional area configured to receive a body part to be imaged using the MRI system;

a frame body extending along a central axis of the frame from the first end toward a second end having a second cross-sectional area smaller than the first cross sectional area;

a plurality of openings formed in the frame body to provide access from an exterior of the frame body to the body part arranged in an interior of the frame;

a conductor coupled to the frame and extending about the frame to form a tapered solenoid shape comprising:

a first loop arranged proximate to the first end of the frame and extending in a first plane substantially transverse to the central axis of the frame;

a second loop arranged proximate to the second end of the frame and extending in a second plane substantially parallel to the first plane and transverse to the central axis of the frame;

at least one leg connecting the first loop and the second loop; and wherein at least a portion of the plurality of openings formed in the frame body is accessible between the first loop and the second loop.

3. The patient support system of claim 2 further comprising a switch to switch between unilateral and bilateral operation.

4. The patient support system of claim 2 further comprising a quad-hybrid circuit configured to allow excitation or reception to be performed with both the first and second coil with an orthogonal phase between the first and second coil to separate the received signals and isolate between the first and second coil.

5. The patient support system of claim 1 wherein the first RF coil is configured to be rotated independently from the bed while the body part to be imaged using the MRI system is arranged in the MRI system.

6. The patient support system of claim 1 wherein the first RF coil is configured to be removable from the bed and replaced with a second RF coil having different cross-sectional areas matched to the body part to be imaged.

7. The patient support system of claim 1 wherein the first RF coil is configured to be rotated independently from the bed to align a desired portion of the body part to be imaged with at least one of the plurality of openings.

8. The patient support system of claim 1 wherein the conductor further comprises a third loop arranged between the first loop and the second loop and extending in a third plane substantially parallel to the first plane and the second plane and transverse to the central axis of the frame.

9. The patient support system of claim 8 wherein the first, second, and third loop are equally displaced from each other along the frame.

10. The patient support system of claim 1 wherein the plurality of openings are configured to receive at least one of a probe and an interventional device.

11. The patient support system of claim 1 wherein the conductor further comprises a third loop arranged between the first loop and the second loop and extending in a third plane substantially parallel to the first plane and the second plane and transverse to the central axis of the frame and wherein the first, second, and third loop are unequally displaced from each other along the frame.

12. The patient support system of claim 1 wherein the frame body is configured to rotate bi-directionally and in a complete circle about the central axis of the frame.

* * * * *